US00PP36343P3

(12) United States Plant Patent
Clarkson

(10) Patent No.: US PP36,343 P3
(45) Date of Patent: Dec. 31, 2024

(54) ***RUBUS* PLANT NAMED 'BWPRASP02'**

(50) Latin Name: *Rubus idaeus*
Varietal Denomination: BWPRASP02

(71) Applicant: BerryWorld Plus Limited., Henley-On-Thames (GB)

(72) Inventor: Graham Clarkson, Faversham (GB)

(73) Assignee: BERRYWORLD PLUS LIMITED., Henley-on-Thames (GB)

( * ) Notice: Subject to any disclaimer, the term of this patent is extended or adjusted under 35 U.S.C. 154(b) by 0 days.

(21) Appl. No.: 18/441,605

(22) Filed: Feb. 14, 2024

(65) Prior Publication Data

US 2024/0397841 P1 Nov. 28, 2024

(30) Foreign Application Priority Data

May 25, 2023 (QZ) ..... PBR2023/1136

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./156, 203, 204
See application file for complete search history.

*Primary Examiner* — Karen M Redden
(74) *Attorney, Agent, or Firm* — Penny J. Aguirre

(57) ABSTRACT

A new cultivar of Raspberry plant named 'BWPRASP02' that is characterized by its early fruit production on floricanes, its berries that are broad conical in shape, large in size and bright medium red in color, its consistent berry size and quality throughout the cropping season, its berries with an extended shelf life, its berries that are easy to pick with low adherence of fruit to receptacle and easily accessible through the canopy, and its versatility in production in being able to planted throughout the year to maintain a regular cropping schedule.

2 Drawing Sheets

Botanical classification: *Rubus idaeus.*
Cultivar designation: 'BWPRASP02'.

CROSS-REFERENCE TO RELATED APPLICATIONS

This application claims priority to European Community Plant Variety Office (CPVO) Plant Breeder's Rights Application No. 2023/1136 filed on May 25, 2023, under 35 U.S.C. 119(f), the entire contents of which is incorporated by reference herein. The application is also related to a Plant Breeder's Rights Application filed in the United Kingdom, No. 18/106, filed Oct. 18, 2023. The information for the plant breeders' rights applications was received directly from the Inventor.

BACKGROUND OF THE INVENTION

The present invention relates to a new and distinct cultivar of red raspberry plant, botanically known as *Rubus idaeus*. 'BWPRASP02' and will be referred to hereinafter by its cultivar name, 'BWPRASP02'. 'BWPRASP02' is a new raspberry plant grown for fresh fruit production.

The new cultivar originated from an ongoing breeding program by the Inventor in Faversham, The United Kingdom. 'BWPRASP02' arose from a cross made in spring of 2013 between a proprietary unpatented selection from the Inventor's breeding program, accession No. CKX-16VF as the female parent and 'Diamond Jubilee' (U.S. Plant Pat. No. 25,455) as the male parent. 'BWPRASP02' was selected as a single unique plant in from amongst the seedlings from the above cross in July of 2013. Subsequent field trials of the new cultivar were conducted in Faversham, The United Kingdom in 2018, 2020, 2021, 2022, and 2023.

Asexual propagation of the new cultivar was first accomplished by the Inventor by root cuttings in winter of 2015 in Faversham, Kent, United Kingdom. Asexual propagation of the new cultivar by root cuttings and tissue culture using meristem tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'BWPRASP02' as a new and unique cultivar of *Rubus.*

1. 'BWPRASP02' exhibits early fruit production on floricanes.
2. 'BWPRASP02' exhibits berries that are broad conical in shape, large in size and bright medium red in color.
3. 'BWPRASP02' exhibits consistent berry size and quality throughout the cropping season.
4. 'BWPRASP02' exhibits berries with an extended shelf life.
5. 'BWPRASP02' exhibits berries that are easy to pick with low adherence of fruit to receptacle and easily accessible through the canopy.
6. 'BWPRASP02' exhibits versatility in production in being able to planted throughout the year to maintain a regular cropping schedule.

The female and male parent of 'BWPRASP02' are both similar to 'BWPRASP02' in having canes with spines. The female parent is also similar in bearing fruit on floricanes.

The female parent of 'BWPRASP02' differs from 'BWPRASP02' in having berries that are less broadly conical in shape, darker red in color, less firmness, higher juiciness borne on thinner canes with a later fruiting period (mid-late season). The male parent of 'BWPRASP02' differs from 'BWPRASP02' in having berries that are round in shape, lighter red in color, less firm, borne on thicker canes, lower juiciness, and a later fruiting period (mid-season) borne on primocanes. 'BWPRASP02' can also be compared to *Rubus ideaus* cultivar 'Sapphire' (U.S. Plant Pat. No. 25,953). 'Sapphire' differs from 'BWPRASP02' in having conical shaped fruit (less broad), higher fruit juice levels, and in producing fruit earlier in the season.

BRIEF DESCRIPTION OF THE DRAWINGS

The accompanying colored photographs illustrate the overall appearance and distinct characteristics of the new *Rubus*. The photographs were taken of plant 16 months in age as grown in a high poly tunnel in 7-L square containers in Faversham, United Kingdom.

The photograph in FIG. 1 provides a view of numerous plants of 'BWPRASP02' with berries.

Figure 1:
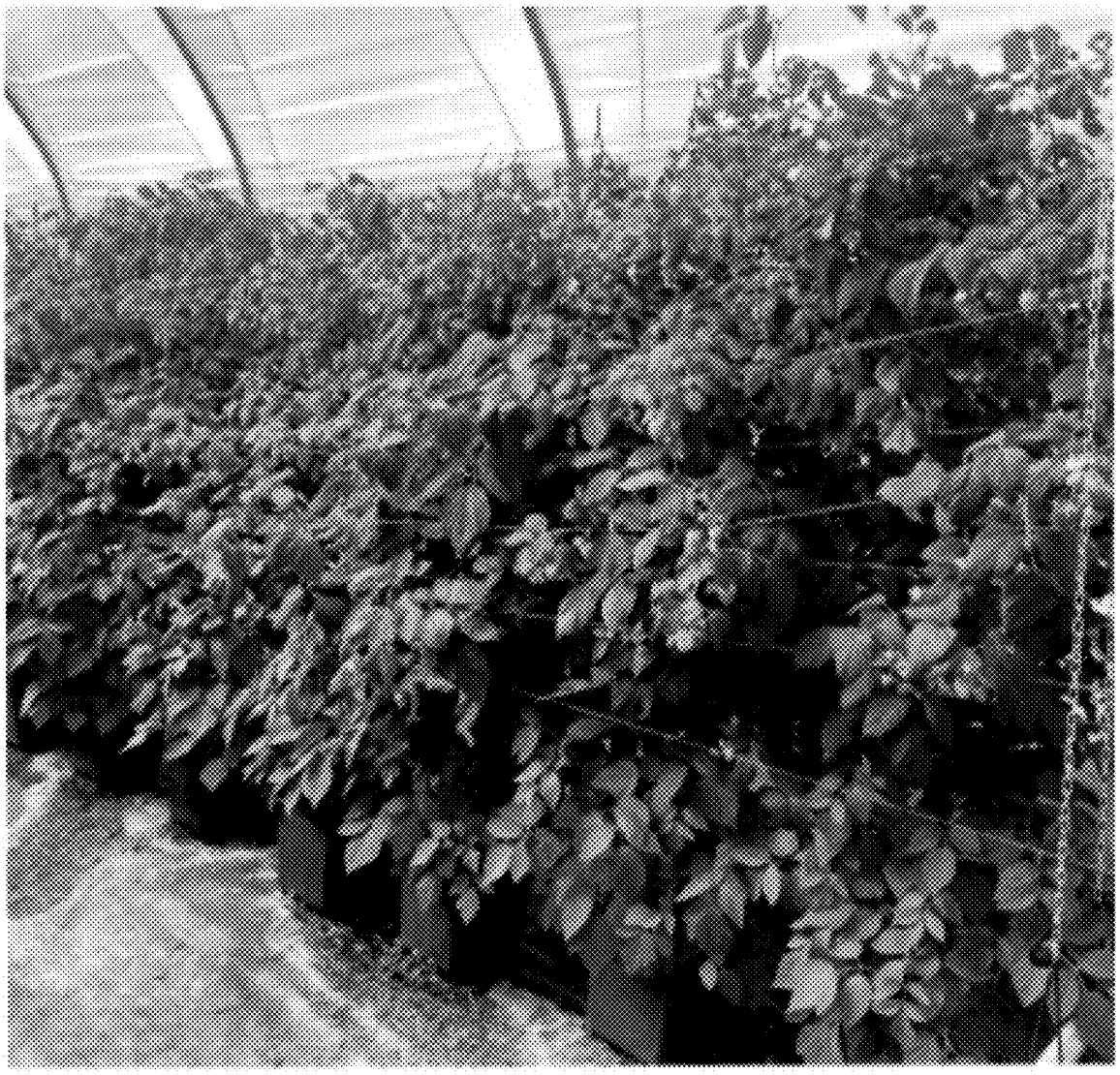
Figure 2:
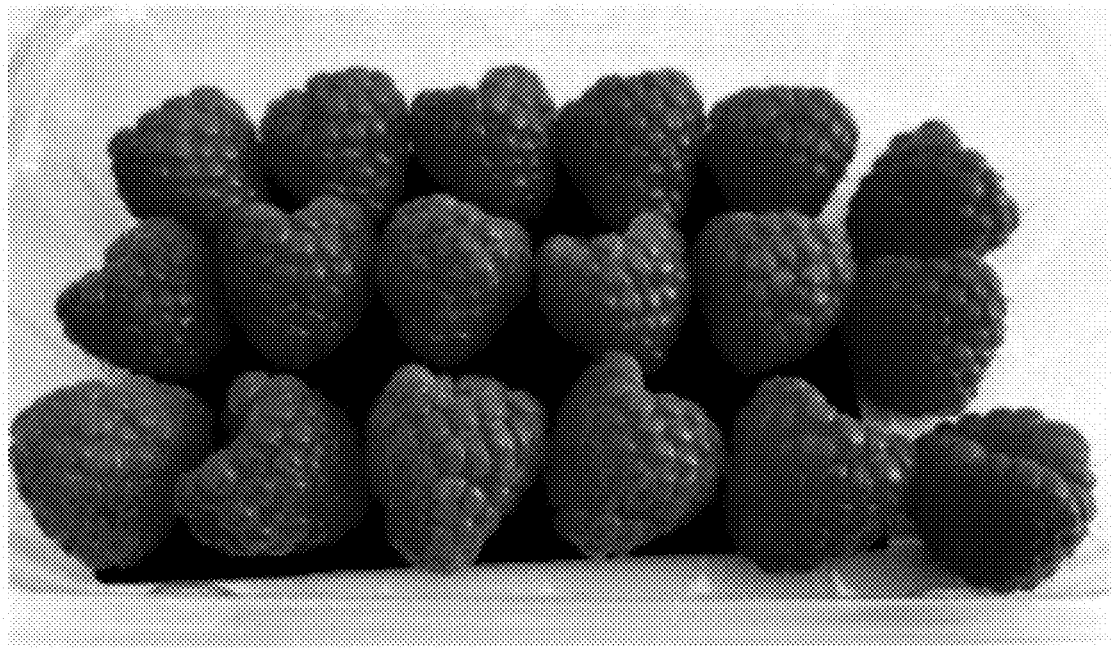

The photograph in FIG. 2 provides a view of the berries of 'BWPRASP02'.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of plants 16 months in age as grown in a poly tunnel in 7-L square containers in Faversham, Kent, The United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Fruit producing perennial.

*Plant habit.*—Floricane, semi-erect.

*Plant shape.*—Broadly conical.

*Height and spread.*—1.65 to 1.95 m in length and average of 97 cm in spread as a 16-month-old plant grown in a container.

*Hardiness.*—This trait has not been fully characterized in a range of cold weather climates but the plants have been successfully grown in England, Spain, The Netherlands, France, and Western Germany. The species is generally cold hardy to at least U.S.D.A Zone 4.

*Diseases and pests.*—No resistance or susceptibility to pests or diseases has been observed.

*Root description.*—Fibrous and vigorous.

*Propagation.*—Tissue culture and root and tip cuttings.

*Root development.*—An average of 2 weeks to root from a cutting, an average of 2 months to fully develop as a young plant with a cane of 2 m reached in about 8 months.

*Growth rate.*—High vigor.

Cane description:

*Fruiting presence.*—On fruiting laterals on floricanes.

*Floricane.*—1.65 to 1.95 m in length (summer), 1.2 cm in diameter, 165A in color, anthocyanin moderate on older canes.

*Fruiting laterals.*—17 to 20 per cane, average of 75 cm in length (at 1 m cane height), no of fruit per lateral cane 25 to 35 (at 1 m cane height).

*No. of current season shoots.*—50 to 75 (during fruiting season).

*Cane internode length.*—6 cm.

*Young shoots.*—142A in color, 50 to 75 shoots per fruiting season, anthocyanin absent, surface glabrous, non-glaucous.

*Spines.*—Linear (needle-like) in shape, on cane; very thin, brittle, and inflexible, 7 mm in length, 3.7 mm in width (at base), density 34 per 5 cm, on laterals; very thin, break at tip, and flexible, 2 mm in length, 5.4 mm in width, density 7 per 5 cm, color; 165C on older canes and laterals, 184A on spawn (emerging primocanes).

Foliage description:

*Time of vegetative bud burst.*—March in Faversham, Kent, The United Kingdom.

*Vegetative bud length.*—Medium.

*Leaf arrangement.*—Alternate.

*Leaf size* (*without petiole*).—20 cm in length, 18 cm in width.

*Leaf division.*—Compound; odd-pinnate, trifoliate.

*Leaf attachment.*—Petiolate.

*Leaflet profile in cross section.*—Slightly concave.

*Leaflet shape.*—Ovate-oblong with elongated point.

*Leaflet overlapping.*—Non-overlapping.

*Leaflet quantity.*—3, 1 terminal and 1 lateral pair.

*Leaflet base.*—Obtuse.

*Leaflet apex.*—Acute aristate-acuminate.

*Leaflet margins.*—Double serrate, lobing absent, low undulation (more undulation on younger leaves).

*Leaflet attachment.*—Sessile.

*Leaflet surface.*—Matte and smooth on both surfaces, rugosity absent.

*Leaflet venation.*—Palmate, mid rib upper surface 147B, lower surface 144A, other veins match leaf color.

*Leaflet color.*—Upper surface 139A, lower surface 191B.

*Leaflet size.*—Lateral leaflets; 10.5 cm in length, 5.28 cm in width, terminal leaflet; an average of 12.02 cm in length and 7.64 cm in width.

*Petioles.*—Round in shape, an average of 5.5 cm in length and 2.3 mm in diameter, upper surface color 144A, lower surface color N144A, moderately strong, surface glabrous.

*Rachis.*—Round in shape, an average of 3.1 cm in length, 1.85 mm in diameter color upper surface 147B, lower surface 144A, surface glabrous.

*Stipules.*—2 per petiole, acicular in shape, an average of 9 mm in length and 0.86 mm in width, upwards orientation, upper surface color 144A, lower surface color N144C.

Inflorescence description:

*Blooming period.*—From May to August in United Kingdom.

*Peduncle.*—Round in shape, color 144B, an average of 4.1 cm in length and 1.5 mm in width, moderate in strength, glabrous surface, 9 to 19 thorns (similar to later spines).

*Pedicels.*—Round in shape, color 144A, an average of 2.9 cm in length and 0.91 mm in width, moderate in strength, glabrous surface.

*Flower type.*—Rotate, single.

*Flower fragrance.*—Faint.

*Flower number.*—25 per lateral.

*Flower diameter.*—1.95 cm.

*Petals.*—*Average of* 5, an average of 7 mm in length, 2.8 mm in width, oblong-spatulate in shapes, base attenuate, apex obtuse, entire margin with slightly undulation, glabrous and matte on upper and lower surfaces, NN155C in color on both surfaces.

*Sepals.*—1.4 mm in length, 1.65 mm in width, broadly ovate in shape, truncate base, broadly acute and notched apex, color both surfaces; center 144A, outer edges 144C and flushed with 179D, surface glabrous and matt on both surfaces.

*Reproductive organs.*—Pistils; 64 to 88 per flower, 155A in color, stamens; 78 to 82 per flower, 155D in color, pollen 199A in color.

Fruit description:

*Productivity* (*yield*).—1.9 kg per cane.

*Self-fruitfulness*.—Self-fertile.

*Fruit size.*—Medium, 2.65 cm in length and 2.53 cm in diameter, length/width ratio 1.05.

*Fruit color.*—Ripe; 44A to 44B, maturing; 37A to 33A, immature; 153A.

*Fruit shape.*—Broad conical.

*Drupes.*—89 to 100/berry, medium in size.

*Fruit surface.*—Glossy, weakly pubescent, slightly creased.

*Fruit maturity date.*—Early season on floricanes.

*Seeds.*—89 to 100/berry, 3.92 mm in length, 1.91 mm in width, kidney-shaped, 161B in color.

*Harvest dates.*—June through August in The United Kingdom.

*Flavor.*—Pleasant and sweet when ripe.

*Fruit weight.*—7.20 g.

*Brix.*—10.6%.

*Titratable acid.*—1.09 (% as citric acid).

*Cavity resistance to deformation.*—High.

*Fruit firmness.*—Firm.

*Adherence to plug.*—Medium, but easy to pick.

*Shelf life.*—Long, an average of 7 days after picking.

*Market use.*—Fresh fruit.

It is claimed:

1. A new and distinct cultivar of Raspberry plant named 'BWPRASP02' as herein illustrated and described.

* * * * *